United States Patent
Egle et al.

(10) Patent No.: US 8,734,470 B2
(45) Date of Patent: May 27, 2014

(54) SURGICAL APPARATUS

(75) Inventors: Walter Egle, Koblach (AT); Martin Erhard, Silbertaler (AT)

(73) Assignee: A.M.I. Agency for Medical Innovations GmbH, Feldkirch (AT)

(*) Notice: Subject to any disclaimer, the term of this patent is extended or adjusted under 35 U.S.C. 154(b) by 273 days.

(21) Appl. No.: 13/029,683

(22) Filed: Feb. 17, 2011

(65) Prior Publication Data

US 2011/0144666 A1 Jun. 16, 2011

Related U.S. Application Data

(63) Continuation of application No. PCT/AT2008/000292, filed on Aug. 19, 2008.

(51) Int. Cl.
*A61B 17/04* (2006.01)

(52) U.S. Cl.
USPC .................. 606/145; 606/144; 606/148

(58) Field of Classification Search
USPC .................. 606/144, 145
See application file for complete search history.

(56) References Cited

U.S. PATENT DOCUMENTS

| | | | |
|---|---|---|---|
| 3,470,875 A | 10/1969 | Johnson | |
| 5,700,266 A * | 12/1997 | Harryman, II | 606/80 |
| 6,077,276 A | 6/2000 | Kontos | |
| 6,428,549 B1 * | 8/2002 | Kontos | 606/144 |
| 6,443,963 B1 * | 9/2002 | Baldwin et al. | 606/148 |
| 6,514,271 B2 * | 2/2003 | Evans et al. | 606/185 |
| 6,893,448 B2 * | 5/2005 | O'Quinn et al. | 606/139 |
| 7,572,265 B2 * | 8/2009 | Stone et al. | 606/139 |
| 7,879,046 B2 * | 2/2011 | Weinert et al. | 606/139 |
| 7,972,344 B2 * | 7/2011 | Murray et al. | 606/144 |
| 8,512,358 B2 * | 8/2013 | Eliachar et al. | 606/144 |
| 2003/0208209 A1 | 11/2003 | Gambale et al. | |
| 2003/0216613 A1 | 11/2003 | Suzuki et al. | |
| 2007/0049952 A1 * | 3/2007 | Weiss | 606/144 |
| 2007/0270885 A1 * | 11/2007 | Weinert et al. | 606/139 |
| 2008/0114382 A1 * | 5/2008 | Mujwid et al. | 606/151 |
| 2008/0147095 A1 | 6/2008 | Gambale | |
| 2011/0028998 A1 * | 2/2011 | Adams et al. | 606/145 |
| 2011/0118760 A1 * | 5/2011 | Gregoire et al. | 606/145 |

FOREIGN PATENT DOCUMENTS

| | | |
|---|---|---|
| EP | 1297787 A1 | 4/2003 |
| EP | 1306056 B1 | 5/2006 |
| WO | 9212674 A1 | 8/1992 |
| WO | 0207609 A2 | 1/2002 |

OTHER PUBLICATIONS

International Search Report for PCT/AT2008/000292, Completed by the European Patent Office on Apr. 23, 2009, 6 Pages.

\* cited by examiner

*Primary Examiner* — Melanie Tyson
*Assistant Examiner* — Todd J Scherbel
(74) *Attorney, Agent, or Firm* — Brooks Kushman P.C.

(57) ABSTRACT

A surgical apparatus, including an instrument, a shaft part with a jaw opening at its distal end and a thread carrier guided by the shaft part displaceable from a retracted position, in which it exposes the jaw opening, and an advanced position, in which it crosses the jaw opening. A thread supported by the thread carrier can be guided through or around human or animal tissue to form a suture or ligature. The thread has a bulge at its end made of the material of the thread so that when the bulge is pushed through a passage opening of the jaw part it elastically deforms and is retained when the thread carrier is retracted.

8 Claims, 5 Drawing Sheets

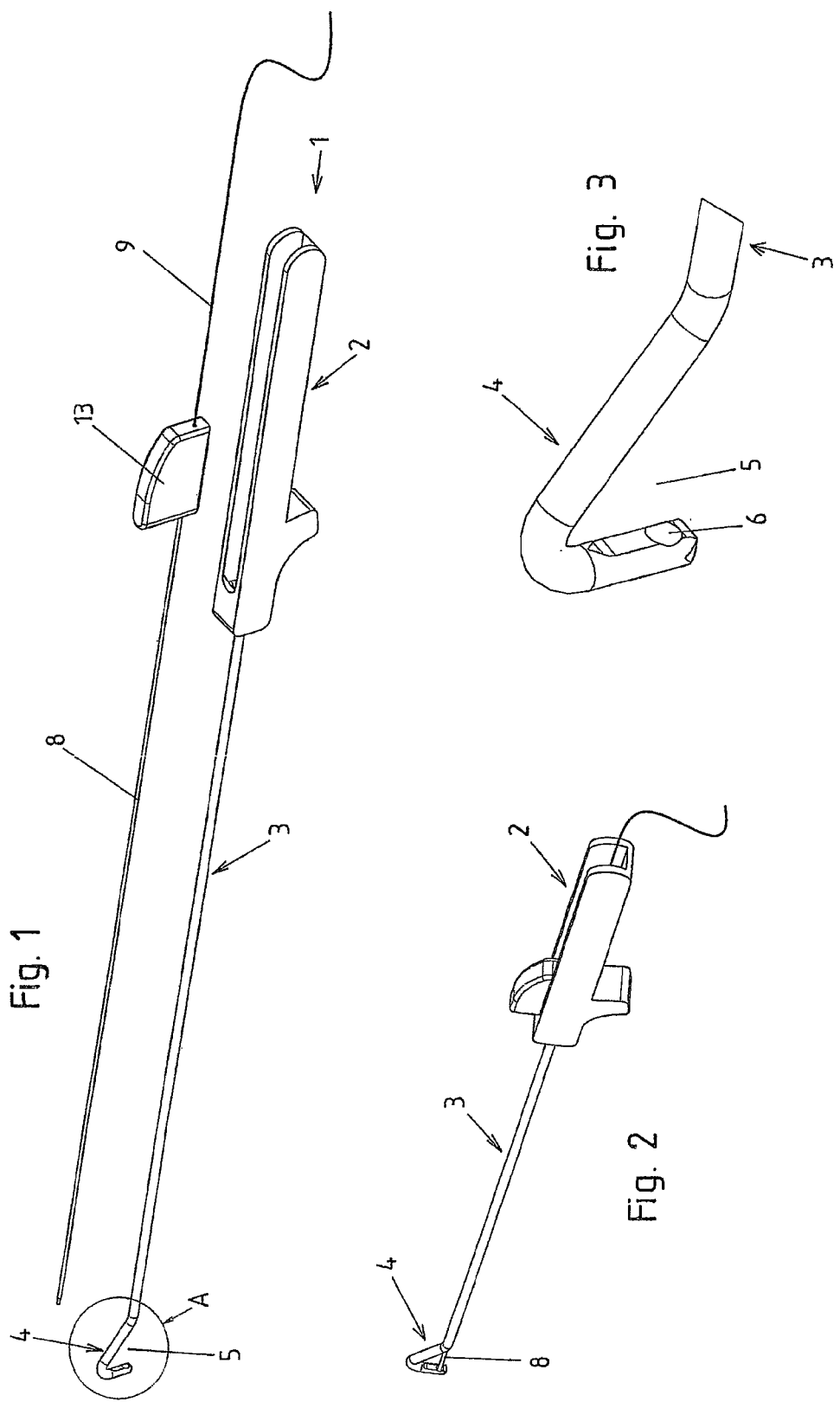

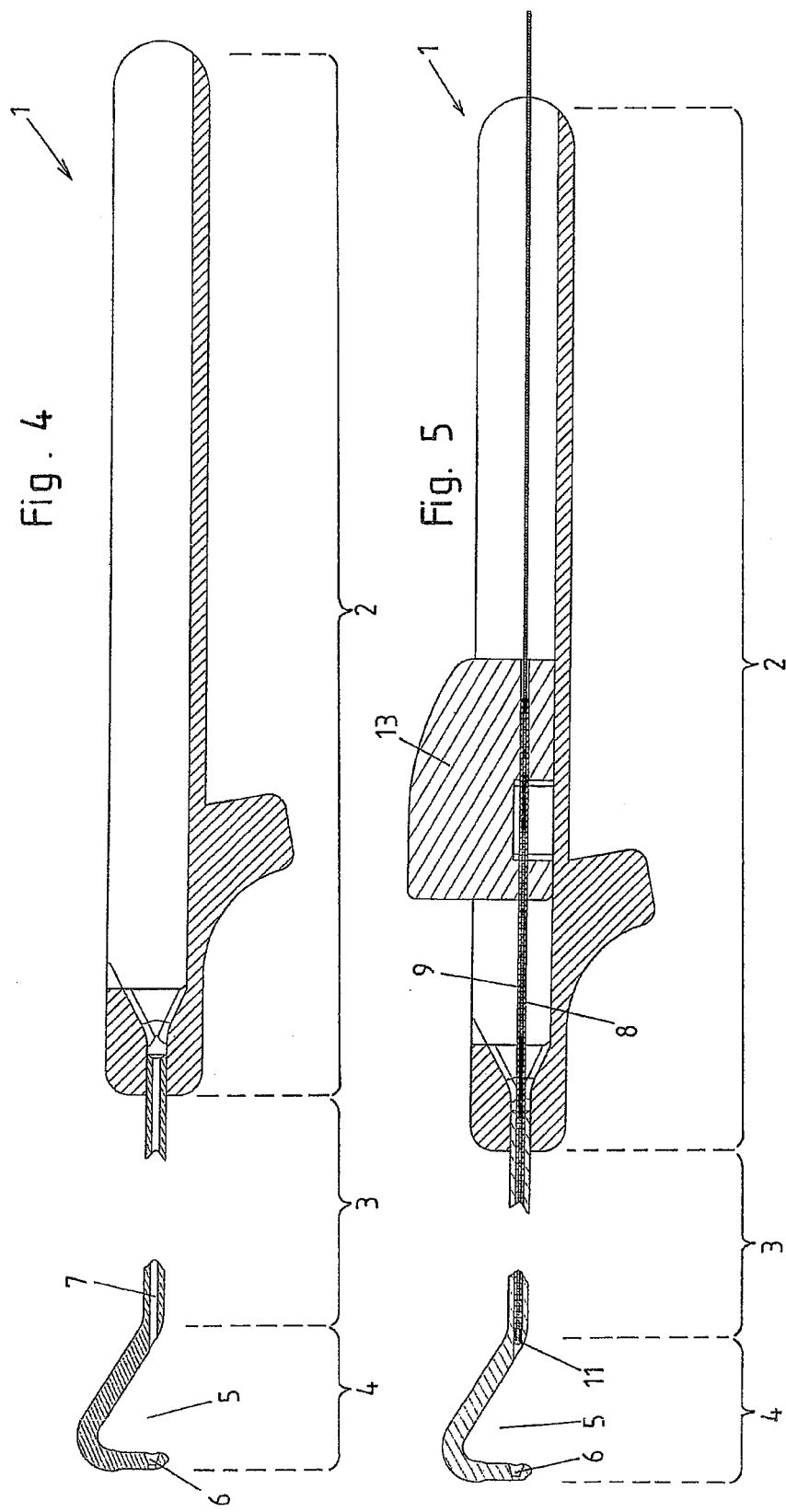

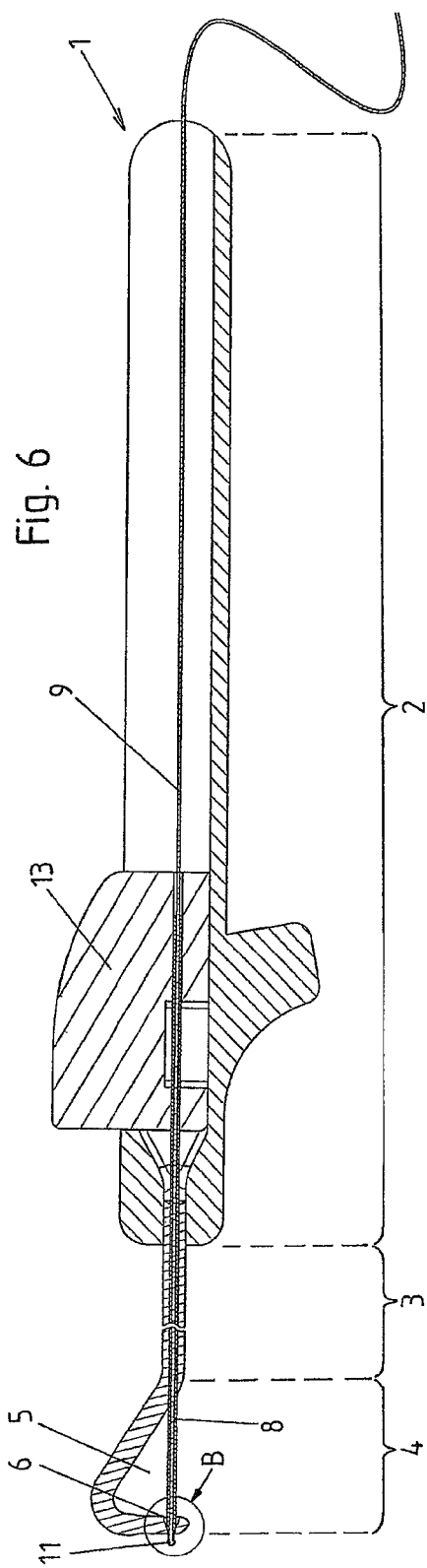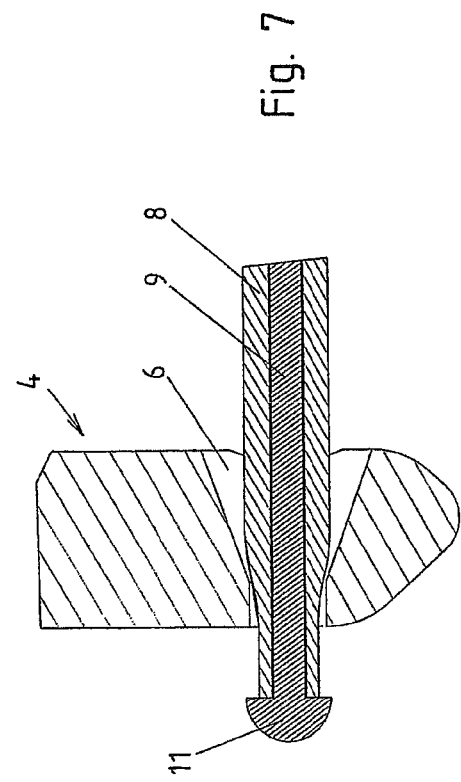

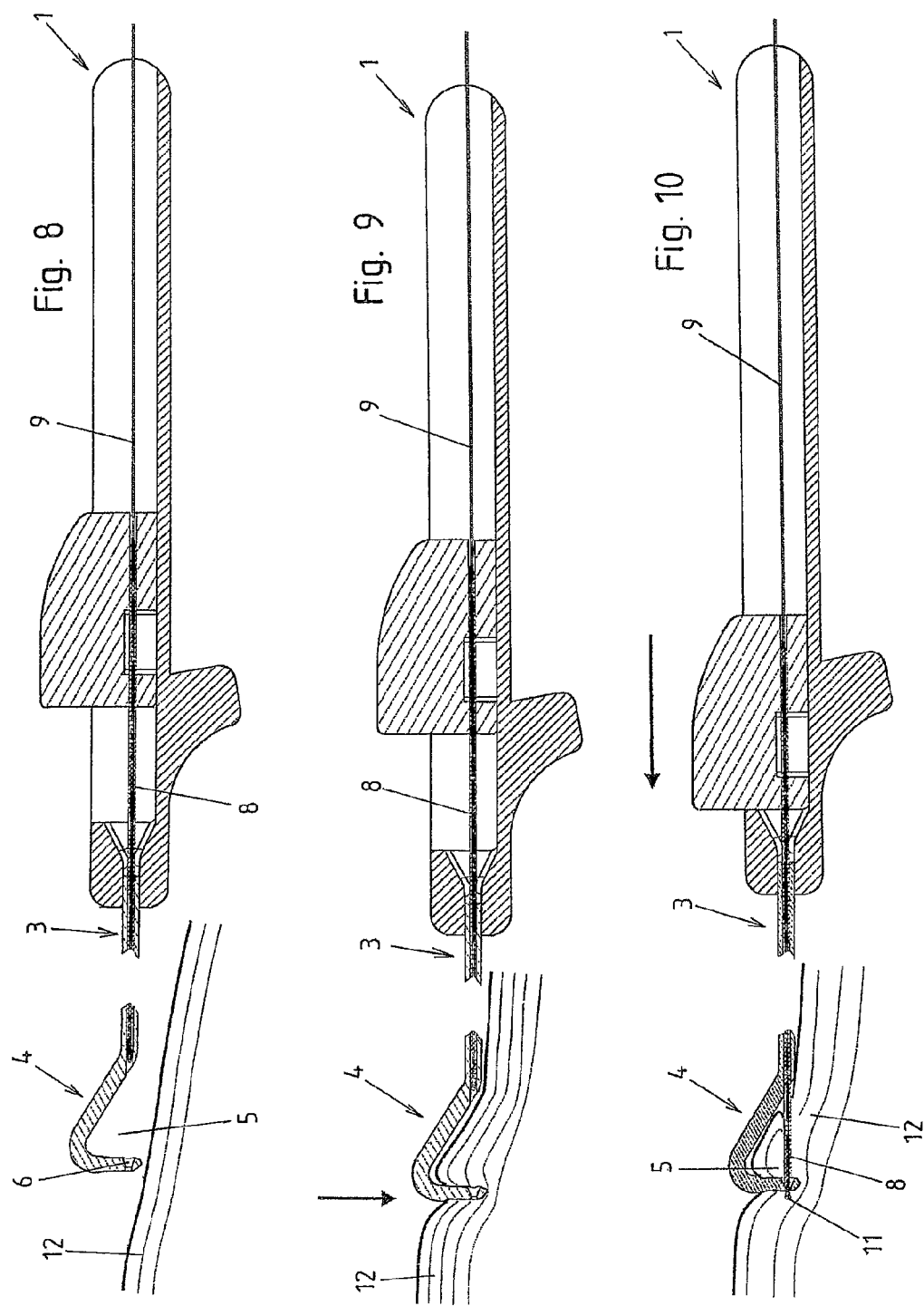

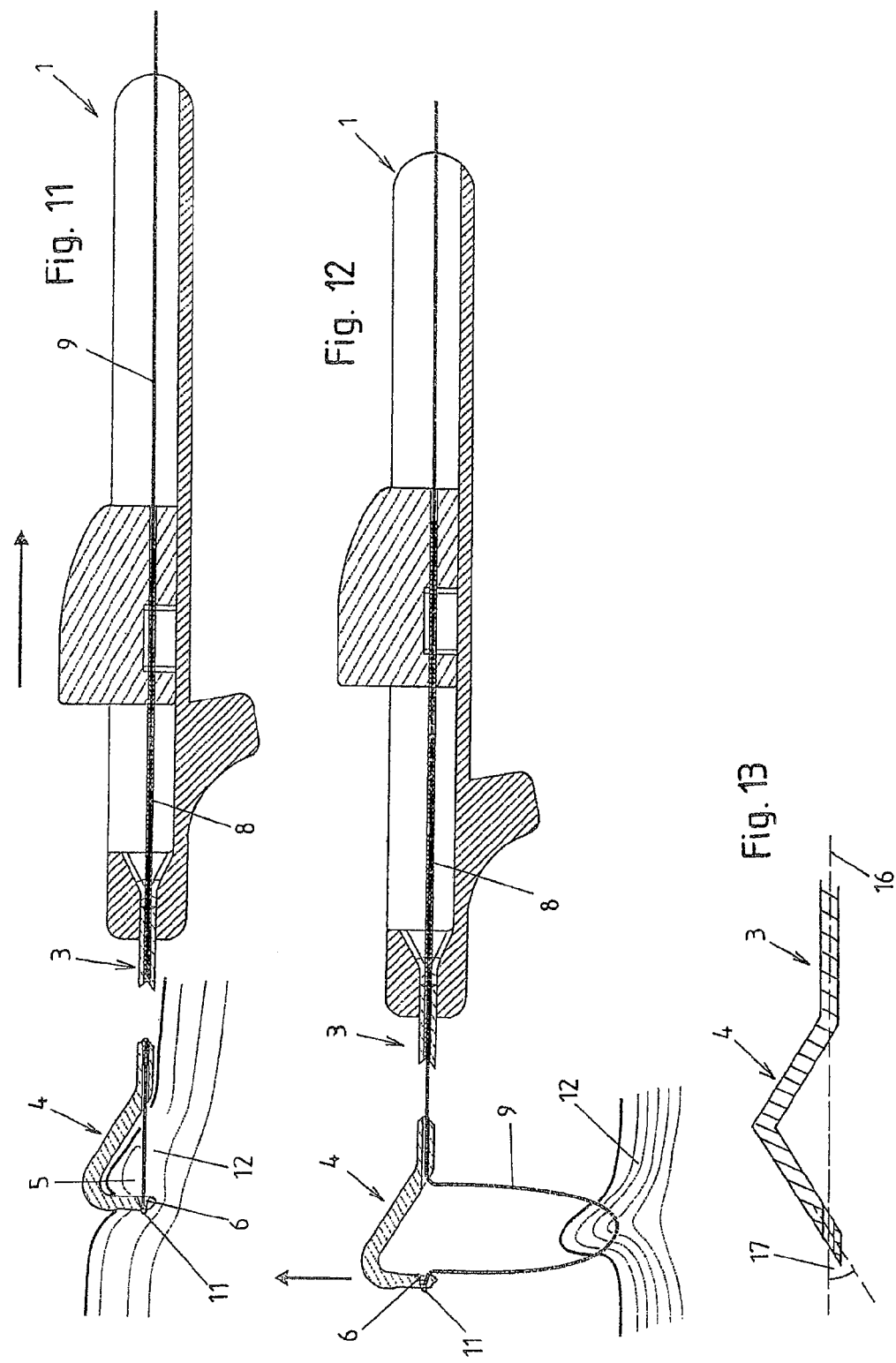

SURGICAL APPARATUS

CROSS-REFERENCE TO RELATED APPLICATIONS

This application is a continuation of PCT/AT2008/000292 filed Aug. 19, 2008, the disclosure of which is incorporated in its entirety by reference herein.

TECHNICAL FIELD

The invention relates to a surgical apparatus comprising an instrument, which has a shaft part and a jaw part with a jaw opening, which jaw part is arranged at a distal end of the shaft part, a thread carrier, which is guided by the shaft part and can be displaced from a retracted position, in which it exposes the jaw opening, into an advanced position, in which it crosses the jaw opening and, with a distal end, protrudes through a passage opening of the jaw part situated distally from the jaw opening, and a thread, which, by means of the thread carrier, can be guided through human or animal tissue, into which a suture should be attached, or guided around human or animal tissue, around which a ligature should be applied.

BACKGROUND

Surgical apparatuses for suturing have been disclosed in various embodiments. There usually is an instrument that can be used to drive a needle, to which the thread has been attached, through the tissue to be sutured, whereupon the needle together with the thread can be pulled through the produced tissue channel, and so the thread is presented for the subsequent ligating. Here the front end of the needle that has been pushed through the tissue is held by a suitable clamping instrument. By way of example, such a suturing apparatus is disclosed in WO 92/12674 A1.

A surgical apparatus of the type mentioned at the outset has been disclosed in EP 1 306 056 B1. A needle can be displaced between a retracted position and an advanced position, in which it crosses a jaw opening in a jaw part of the instrument and protrudes through a passage opening in the jaw part situated distally from the jaw opening. The needle has a type of barbed hook that, when said needle is subsequently retracted, is used to carry along a loop of the thread that crosses the jaw opening in the jaw part, and so the needle constitutes a thread carrier. One of the two thread ends can subsequently be pulled through the tissue, whereupon the thread is presented for the subsequent ligating. A disadvantage of this apparatus is the relatively complicated handling. Furthermore, an appropriate size of the channel produced in the tissue is required for pulling back the needle with the hooked-in thread loop, and this leads to a corresponding injury.

A further surgical apparatus of the type mentioned at the outset has been disclosed in one of the exemplary embodiments described in WO 02/07609 A2. Here, an armoring part has been fixed to the end of the thread, the former being designed as a needle tip, which is carried along by the thread carrier when said thread carrier is displaced into its advanced position from its retracted position. A section of the jaw part situated distally from the jaw opening is, on its end side, designed with a snap-lock mechanism for the armoring part, which snap-lock mechanism is made of fork-like projections at the end of the jaw part. After pressing the armoring part through the passage opening, said armoring part is secured against being retracted by this snap-lock mechanism.

SUMMARY

An object of the invention is to provide an apparatus of the type mentioned at the outset that can be handled more easily.

According to the invention, this is achieved by a surgical apparatus, comprising:

an instrument, which has a shaft part and a jaw part with a jaw opening, which jaw part is arranged at a distal end of the shaft part, a thread carrier, which is guided by the shaft part and can be displaced from a refracted position, in which it exposes the jaw opening, into an advanced position, in which it crosses the jaw opening and, with a distal end, protrudes through a passage opening of the jaw part situated distally from the jaw opening, and a thread, which, by means of the thread carrier, can be guided through human or animal tissue, into which a suture should be attached, or guided around human or animal tissue, around which a ligature should be applied, wherein the thread, on its end side, has a bulge, which bulge is made of the material of the thread and is carried along by the thread carrier when said thread carrier is displaced into its advanced position from its retracted position, wherein the bulge is pushed through the passage opening of the jaw part under at least partial elastic deformation of the bulge.

In the apparatus according to the invention, a bulge made of the material of the thread is formed at the end side of the thread, which bulge is carried along by the thread carrier when the latter is displaced into its advanced position from its retracted position. Here, the bulge is pushed through the passage opening in the jaw part, wherein the bulge partly or wholly deforms elastically or there is a combination of the aforementioned deformation of the bulge in the thread and a partial or whole elastic deformation of a material partly or wholly delimiting the passage opening in the jaw part. If the thread carrier is subsequently retracted again, the bulge arranged on the thread is retained by the edge of the passage opening in the jaw part, i.e. it is not returned with the thread carrier. When the instrument is subsequently refracted, the thread is presented for threading the suture or guided around the tissue for ligating.

Hence the apparatus according to the invention makes it very simple to present a thread for a suture or to guide the thread around the tissue for making a ligature. If the thread should be guided through the tissue, there is only little injury to the tissue because the puncture channel produced in the tissue can be very small.

The thread carrier advantageously has a tubular design, wherein the thread runs through the inner channel of the tube and the bulge arranged on the thread is situated in front of the distal end of the tube and, in this case, the external diameter of the bulge is greater than the internal diameter of the channel such that the bulge cannot be retracted through the channel. Hence, when the thread carrier is advanced, the end of the thread with the bulge is carried along by the thread carrier. When the thread carrier is refracted, the thread can partly or wholly be pulled out of the distal end of the channel.

The thread carrier is preferably guided in an inner channel of the shaft part of the instrument, wherein said thread carrier is, in the retracted position, arranged in the inner channel of the shaft part together with the bulge arranged on the thread. When the thread carrier is displaced into its advanced position, it protrudes from the inner channel with an end section, which crosses the jaw opening of the jaw part. After the bulge arranged on the thread is "hooked into" the passage opening of the jaw part, the thread carrier is again retracted to the extent that it is situated within the channel in the shaft part or until it has been pulled out of the latter on the proximal side.

The bulge arranged at the end of the thread and carried along when the thread carrier is advanced is made of the material of the thread itself. In the case of a thread made of a plastic that can be fused, the bulge can be formed by fusing the end of the thread such that a thickened head is produced. There are conventional surgical threads that consist of such a plastic that can be fused. A further variant consists of deforming the end of the thread, e.g. by simple folding, and keeping it in this deformation (e.g. by adhesive bonding) such that a bulge is formed.

An apparatus according to the invention can serve to affix a surgical suture, more particularly a simple interrupted suture, wherein the thread is presented by the surgical apparatus according to the invention, i.e. it is guided through the tissue to be sutured. Additionally, or as an alternative thereto, such a surgical apparatus can serve for ligating in human or animal tissue, i.e. for tying off acrochordon-like structures, vessels or other hollow organs, wherein the thread is guided around the tissue to be tied off.

When this document refers to "proximal" and "distal", this describes the position with respect to the operator; a distal part is situated further away from the operator than a part that is proximal thereto. Furthermore, a movement from proximal to distal is referred to as forwards and a reverse movement is referred to as backwards or directed backwards.

Further advantages and details of the invention are explained in the following text with the aid of the attached drawing.

BRIEF DESCRIPTION OF THE DRAWINGS

FIG. 1 shows an oblique view of an instrument and a thread carrier to be inserted therein, with a thread inserted into the latter, as per a possible embodiment of the invention;

FIG. 2 shows an oblique view of the apparatus illustrated in FIG. 1 from a different point of view, wherein the carrier has been inserted into the instrument and is in its advanced position;

FIG. 3 shows a magnified detail A from FIG. 1;

FIG. 4 shows a longitudinal central section through the instrument, without the inserted carrier;

FIG. 5 shows a longitudinal section corresponding to FIG. 4, with an inserted and thread-loaded carrier, which is in its retracted position;

FIG. 6 shows a longitudinal section that is analogous to FIG. 5, but in the advanced position of the carrier;

FIG. 7 shows a magnified detail B from FIG. 6;

FIG. 8 to 12 show illustrations for clarifying the individual steps when presenting a thread, wherein the apparatus is illustrated in a longitudinal central section in each case;

FIG. 13 shows a schematic illustration of a distal end section of the instrument as per a further embodiment variant of the invention.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

In the following text, a first exemplary embodiment of the invention will be explained with the aid of FIGS. 1 to 12. The apparatus comprises an instrument 1 with a gripper part 2, by means of which the instrument can be held; an elongated, preferably straight, shaft part 3; and a jaw part 4 arranged at the distal end of the shaft part 3, said jaw part having a jaw opening 5. With respect to the longitudinal axis 16 of the shaft part 3, the jaw opening 5 opens to the side (i.e. not to the front).

An inner channel 7 runs through the shaft part 3 and through the jaw part 4, up to the jaw opening 5. Thus, the channel 7 at its distal end opens into the jaw opening 5 and is likewise open at its proximal end, which can be situated at the proximal end of the shaft part 3 or in the vicinity of the gripper part 2. In accordance with the straight design of the shaft part 3, the channel 7 runs in a straight line, and, in the straight-line continuation of the channel 7, distally from the jaw opening 5, there is a passage opening 6 that pierces a distal section of the jaw part 4 in a straight line and parallel to the direction of longitudinal extent of the shaft part 3, starting in the vicinity of the jaw opening 5.

In the illustrated exemplary embodiment, the jaw part 4 and the shaft part 3 are formed from a common shaft of the instrument, the end section of which has a bent profile for forming the jaw part 4. Here the profile comprises first and second bends in opposite directions for forming the jaw opening 5. The passage opening 6 is arranged in the end section of the shaft situated opposite to the opening of the channel 7, which end section is at an angle, for example almost perpendicular, to the channel 7.

A tubular thread carrier 8 can be inserted into the channel 7; to be precise from the proximal end of the channel 7. The thread carrier 8 illustrated in FIGS. 1, 2 and 5-7 is loaded with a thread 9. Here the thread 9 extends through an inner thread channel 10 of the thread carrier 8. At its front end, the thread 9 has a bulge 11, which is situated in front of the distal end of the thread channel 10 and, in the process, is so large that it cannot be pulled into the thread channel 10. By way of example, the bulge 11 can consist of the thread 9 material, wherein it is formed by fusing the plastic material of the thread 9. The rear end of the thread 9 can protrude from the proximal end of the thread channel 10, as illustrated, or else it can be situated within the thread channel 10.

The distal end of the thread carrier 8 can be tapered, and so the thread carrier 8 is designed like a hollow needle; this makes piercing the tissue easier.

The thread carrier 8 can be displaced into an advanced position (FIG. 6) from a refracted position (FIG. 5) along the direction of the longitudinal axis 16 of the shaft part 3. The distal end of the thread carrier 8 is situated within the channel 7 of the instrument 1 in the retracted position. In the illustrated exemplary embodiment, the distal end of the thread carrier 8 can be refracted arbitrarily far into the channel 7 or, in order to enable complete separation of the thread carrier 8 from the instrument 1, it can be pulled out of the proximal end of the channel 7.

In the advanced position of the thread carrier 8, an end section of the latter protrudes from the channel 7, wherein this end section crosses the jaw opening 5 and protrudes through the passage opening 6 with its proximal end.

When the carrier 8 is displaced into its advanced position from its retracted position, the thread carrier 8 carries along the bulge 11 and guides the latter through the passage opening 6. The bulge is compressed in the process. The deformation of the bulge 11 is at least partly elastic in this case. Hence, after the bulge 11 passes through the passage opening 6, it reexpands such that it has a larger diameter than the passage opening 6 in the distal region of the opening and is held against being retracted through the passage opening 6 during a subsequent retraction of the thread carrier 8. Thus, when the thread carrier 8 is retracted, the distal end of the thread 9 is pulled out of the distal end of the thread carrier 8.

The opening of the passage opening 6, which faces the jaw opening 5 and is in the section of the jaw part 4 situated distally from the jaw opening 5, opens up in order to obtain a larger tolerance for inserting the thread carrier 8. More particularly, this forms a type of inlet cone for the thread carrier 8.

An actuation part 13 attached to the thread carrier 8 is used to displace the latter in the illustrated exemplary embodiment.

FIGS. 8 to 12 illustrate the application of the apparatus for presenting a thread for forming a surgical simple interrupted suture. After the free end of the section of the jaw part 4, which is situated distally from the jaw opening 5, has the passage opening 6 and is designed as a piercing tip, was made to approach the human or animal tissue 12 in which the suture is intended to be produced (FIG. 8), the section of the jaw part 4 situated distally from the jaw opening 5 is pierced into the tissue 12, as can be seen in FIG. 9. As a result, tissue 12 reaches the vicinity of the jaw opening 5. Here the thread carrier is in a retracted position, in which the distal end thereof lies within the channel 7.

Subsequently, the thread carrier 8 is displaced distally (=forwards) by pushing the actuation part 13 forwards, with the thread 9 being taken along in the process. The distal end of the thread carrier 8 and the bulge 11 in the thread 9 situated in front of it pierce through the tissue 12, with a passage channel being produced for the thread 9. The thread carrier 8 is displaced until it reaches its advanced position, illustrated in FIG. 10, in which it passes through the passage opening 6 in the distal section of the jaw part 4, as illustrated in FIG. 10. As a result, the bulge 11 in the thread 9 was pushed through the passage opening 6.

Subsequently, the thread carrier 8 is in turn displaced into a retracted position, in which the distal end thereof is situated in the channel 7, as illustrated in FIG. 11. This may be the original retracted position or another retracted position (i.e. the distal end of the thread carrier 8 is situated at a different position than prior to the advance). In the process, the bulge 11 in the thread is retained by the distal section of the jaw part 4, i.e. it does not move back through the passage opening 6. Hence the thread 9 remains stationary when the thread carrier 8 is retracted, wherein said thread is pulled through the thread channel 10 of the thread carrier 8. The situation after the refraction of the thread carrier 8 is illustrated in FIG. 11.

In the illustrated exemplary embodiment, the thread carrier 8 is retracted by the actuation part 13. By way of example, it is also feasible and possible for the thread carrier 8 to be acted upon by at least one spring element such that the thread carrier 8 can be displaced by this at least one spring element into a refracted position, in which the distal end of said thread carrier is within the channel 7, from its advanced position.

The jaw part 4 is subsequently pulled out of the tissue 12. Here the bulge 11 is still retained by the distal section of the jaw part 4. Hence the thread 9 is pulled through the tissue channel, wherein said thread is furthermore pulled through the thread channel 10 of the thread carrier 8 and out of the channel 7 of the instrument 1. This situation is illustrated in FIG. 12. The instrument 1 is continued to be pulled out until the two thread ends protruding from the tissue channel are long enough. At least the end of the thread adjoining the bulge 11 is subsequently cut off and, should the other end of the thread not yet have been pulled out of the instrument 1 in its entirety, it is also cut off. The thread now is presented, whereupon the operator can tie the knot of the simple interrupted suture.

When the thread carrier 8 is retracted into its advanced position after the advance, this refraction can also continue further than illustrated in FIG. 11. Here the thread carrier 8 can also be pulled completely out of the channel 7 and can be separated from the instrument 1, wherein the thread 9 is completely pulled out of the thread channel 10 of the thread carrier 8.

If the simple interrupted suture to be produced should comprise a plurality of individual threads with respective knots, the above-described procedure is repeated. By way of example, a new apparatus can be used to this end for each thread 9 to be presented, in which apparatus the thread carrier 8 is loaded with a thread 9. Another option consists of completely pulling the thread carrier 8 out of the instrument for each thread 9 to be presented, and to replace said thread carrier by a new thread carrier, which is loaded with a thread 9 and inserted into the channel 7 from the proximal direction. A further option consists of completely pulling the thread carrier 8 out of the instrument 1 for each thread 9 to be presented and to load it with a new thread 9.

The free end of the section of the jaw part 4 situated distally of the passage opening 6, which section can also be referred to as a prong, is designed as a piercing tip for piercing into the tissue 12, as described above. Here, a piercing tip such as this can have various designs. As illustrated, the design can be in the form of a blunt tip, with different modifications being possible in this case. On the other hand, the design can also be in the form of a cutting tip. By way of example, such cutting tips can be shaped like a cone, a pyramid or a knife cutting-edge.

If an apparatus according to the invention is used for ligating, the tissue to be tied off is inserted into the jaw opening 5 of the jaw part 4. Hence, depending on the application, piercing of the tissue can be dispensed with. A design of the distal, free end of the jaw part 5 as a piercing tip is not required in this case. After the tissue has been inserted into the jaw opening 4, the thread carrier 8 is displaced into its advanced position from its retracted position; then it is retracted again until at least its distal end is situated in the channel 7 and the instrument 1 is subsequently lifted from the tissue to be tied off After the appropriate severing of the thread, the thread is placed around the tissue to be tied off The tying off can take place thereafter. Hence the steps are analogous to those described with the aid of FIGS. 8 to 12, wherein, however, the thread is pulled around the tissue and not through a tissue channel.

A combination of an elastic deformability of the material at least in part delimiting the passage opening 6 and an elastic deformability of the bulge 11 is also feasible and possible.

It is also feasible and possible for only part of the inner circumference of the bore in the base part to be lined with an elastic material.

In the exemplary embodiment illustrated in FIGS. 1 to 12, the piercing tip of the jaw part 4 is inserted into the tissue 12 perpendicularly to the longitudinal axis of the shaft part 3. FIG. 13 shows an embodiment variant, in which the jaw part 4 can be inserted into the tissue 12 by a movement in the direction of the longitudinal axis 16 of the shaft part 3. An end section of the jaw part 4 adjoining the distal end of the jaw part 4 in this case includes an angle 17 with the longitudinal axis 16 that is smaller than 60°, preferably smaller than 45°.

The tissue 12, through which the thread 9 is presented for forming a simple interrupted suture or around which the thread 9 is guided for ligating, can be e.g. a muscle, parenchyma, a tendon or another type of soft tissue (i.e. not e.g. bone) that can be found in the body.

An apparatus according to the invention can, in particular, be designed for use in minimally invasive surgery, more particularly e.g. in laparoscopy. Here, the jaw part 4 is designed such that it can be passed through a trocar. Trocars usually have internal diameters in the region of 5 mm to 25 mm. The shaft part 3 has a sufficient length so that it can be guided up to the site of the surgery.

Overall, an apparatus according to the invention can be designed as a disposable instrument. The option of completely pulling the thread carrier 8 out of the channel 7 can be dispensed with in this case because the instrument 1 with the thread carrier 8 is disposed once the thread 9 has been placed.

A second option consists of designing the instrument 1 as a reusable instrument, in which the thread carrier 8 however can only be used once. Here the instrument 1 consists of a sterilizable material, more particularly steam-sterilizable material, preferably stainless steel. Once a thread 9 has been placed, the thread carrier 8 is separated from the instrument 1 and a new thread carrier 8, which is loaded with a thread 9, is inserted.

In a further option, both the instrument 1 and the thread carrier 8 together with the parts attached thereto (the actuation part 13 in the illustrated exemplary embodiment) are designed as reusable parts. To this end, they can be sterilized, more particularly steam-sterilized, and consist of a material that is suitable for this purpose, e.g. stainless steel. After a thread 9 has been placed, the thread carrier 8 is separated from the instrument 1 and loaded with a new thread 9. There can be a plurality of thread carriers 8 for any given instrument 1, which thread carriers can be used alternately.

Different modifications of the described exemplary embodiments are feasible and possible without departing from the scope of the invention. Thus, for example, the jaw part 4 could also be designed differently than as a bent end section of a shaft, for example as a separate part attached to the shaft part 3.

Rather than guiding the thread carrier 8 though a channel 7 in the instrument 1, the thread carrier 8 could also be guided on the outside of the shaft part 3. Here, the distal end of the thread carrier 8 would, in the retracted position, again be arranged proximally to the jaw opening 5 such that the jaw opening 5 is exposed.

A circular-arc-shaped design of the shaft part 3 and the thread carrier 8 would also be feasible and possible.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. Surgical apparatus, comprising:
    an instrument, which has a shaft part and a jaw part with a jaw opening, which jaw part is arranged at a distal end of the shaft part;
    a thread carrier, which is a tube with an inner thread channel extending therethrough and opening at a distal end of the thread carrier; the thread carrier is guided by the shaft part and can be displaced from a retracted position, in which it exposes the jaw opening, into an advanced position, in which it crosses the jaw opening and, with the distal end, protrudes through a passage opening of the jaw part situated distally from the jaw opening;
    a thread, which, by means of the thread carrier, can be guided through human or animal tissue, into which a suture should be attached, or guided around human or animal tissue, around which a ligature should be applied; and
    wherein the thread extending through the inner thread channel has, on its end side, a bulge formed in the thread, which bulge is situated in front of the distal end of the thread carrier and has an external diameter which is greater than an internal diameter of the inner thread channel and greater than an internal diameter of a distal region of the passage opening, so that the bulge cannot be pulled into the thread channel and is carried along by the thread carrier when said thread carrier is displaced into its advanced position from its retracted position, wherein the bulge is pushed through the passage opening of the jaw part under at least partial elastic deformation of the bulge and the bulge is held distal to the passage opening and against being retracted through the passage opening during a subsequent retraction of the thread carrier.

2. Surgical apparatus according to claim 1, wherein the thread carrier is guided in an inner channel running through the shaft part and, in its advanced position, protrudes from the inner channel with an end section, which crosses the jaw opening.

3. Surgical apparatus according to claim 2, wherein the thread carrier can be pulled out of a proximal end of the inner channel of the shaft part in its entirety.

4. Surgical instrument according to claim 1, wherein the jaw part is formed by a bent end section of a shaft of the instrument, which end section also forms the shaft part of the instrument.

5. Surgical apparatus according to claim 1, wherein the jaw opening of the jaw part opens towards a lateral side with respect to a longitudinal extent of the shaft part.

6. Surgical apparatus according to claim 1, wherein an end of the jaw part situated distally from the jaw opening is designed as an insertion tip for piercing into the tissue into which the suture should be attached.

7. Surgical apparatus according to claim 1, wherein the passage opening in the jaw part opens up towards the jaw opening.

8. Surgical apparatus according to claim 1, wherein a material, which at least partly delimits the passage opening in the jaw part, also at least in part deforms elastically when the bulge is pushed through the passage opening of the jaw part.

* * * * *